US008101744B2

(12) United States Patent
Birkner et al.

(10) Patent No.: US 8,101,744 B2
(45) Date of Patent: Jan. 24, 2012

(54) ISOLATION AND PURIFICATION OF NUCLEIC ACIDS WITH A SOLID PHASE

(75) Inventors: Christian Birkner, Uffing (DE); Herbert Von der Eltz, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 532 days.

(21) Appl. No.: 12/105,556

(22) Filed: Apr. 18, 2008

(65) Prior Publication Data

US 2008/0319182 A1    Dec. 25, 2008

(30) Foreign Application Priority Data

Apr. 20, 2007  (EP) .................................... 07008073

(51) Int. Cl.
*C07H 21/00* (2006.01)
(52) U.S. Cl. .................. 536/25.4; 536/25.41; 536/25.42
(58) Field of Classification Search ................. 536/25.4, 536/25.41, 25.42
See application file for complete search history.

(56) References Cited

U.S. PATENT DOCUMENTS

| 4,683,195 | A | 7/1987 | Mullis et al. |
|---|---|---|---|
| 5,130,238 | A | 7/1992 | Malek et al. |
| 5,808,041 | A | 9/1998 | Padhye et al. |
| 6,858,720 | B2 | 2/2005 | Myerson et al. |
| 2004/0121336 | A1 | 6/2004 | Greenfield et al. |
| 2004/0180445 | A1 | 9/2004 | Domanico et al. |

FOREIGN PATENT DOCUMENTS

| DE | 3724442 A1 | 2/1989 |
|---|---|---|
| EP | 0281390 B1 | 6/1994 |
| EP | 0439182 B1 | 4/1996 |
| EP | 1234832 A2 | 8/2002 |
| EP | 0818461 B1 | 9/2005 |
| EP | 1736542 A1 | 12/2006 |
| WO | 90/01069 A1 | 2/1990 |
| WO | 92/00880 A1 | 1/1992 |
| WO | 96/18731 A3 | 6/1996 |
| WO | 99/61603 A1 | 12/1999 |
| WO | 00/69872 A3 | 11/2000 |
| WO | 01/94573 A3 | 12/2001 |
| WO | 02/48164 A3 | 6/2002 |
| WO | 2005/064010 A1 | 7/2005 |

OTHER PUBLICATIONS

Xie et al. Tetrahedron Letters (2004), vol. 45, pp. 2013-2015.*
Katsyuba et al. Helvetica Chimica Acta (2004), vol. 87, pp. 2556-2565.*
European Search Report issued Nov. 7, 2007 in European Application No. 07008073.4.
Abramson, Richard D. and Myers, Thomas W., Nucleic acid amplifiction technologies, Current Opinion in Biotechnology, 1993, pp. 41-47, vol. 4.
Barany, Francis, The Ligase Chain Reaction in a PCR World, PCR Methods and Applications, 1991, pp. 5-16, vol. 1.

Barany, Francis, Genetic disease detection and DNA amplification using cloned thermostable ligase, Proceedings of the National Academy of Sciences USA, Jan. 1991, pp. 189-193, vol. 88.
Berensmeier, Sonja, Magnetic particles for the separation and purification of nucleic acids, Applied Microbiology and Biotechnology, 2006, pp. 495-504, vol. 73.
Boom, R. et al., Rapid and Simple Method for Purification of Nucleic Acids, Journal of Clinical Microbiology, Mar. 1990, pp. 495-503, vol. 28, No. 3.
Chomczynski, Piotr and Sacchi, Nicoletta, Single-Step Method of RNA Isolation by Acid Guanidinium Thiocyanate-Phenol-Chloroform Extraction, Analytical Biochemistry, 1987, pp. 156-159, vol. 162.
Danenberg, Peter V. and Santi, Daniel V., Inhibition of Phenylalanyl-tRNA Synthetase by Aromatic Guanidines and Amidines, Journal of Medicinal Chemistry, 1975, pp. 582-530, vol. 18, No. 5.
Dore, Kim et al., Fluorescent Polymeric Transducer for the Rapid, Simple, and Specific Detection of Nucleic Acids at the Zeptomole Level, Journal of the American Chemical Society, 2004, pp. 4240-4244, vol. 126.
Guatelli, John C. et al., Isothermal, in vitro amplification of nucleic acids by a multienzyme reaction modeled after retroviral replication, Proceedings of the National Academy of Sciences USA, Mar. 1990, pp. 1874-1878, vol. 87.
Inagami, Tadashi, The Alkylation of the Active Site of Trypsin with Iodoacetamide in the Presence of Alkylguanidines, The Journal of Biological Chemistry, Aug. 1965, PC3453-PC3455, vol. 240, No. 8.
Jakobi, R. et al., Filter-Supported Preparation of λ Phase DNA, Analytical Biochemistry 1988, pp. 196-201, vol. 175.
Kwoh, D. Y. et al., Transcription-based amplification system and detection of amplified human immunodeficiency virus type 1 with a bead-based sandwich hybridization format, Proceedings of the National Academy of Sciences, Feb. 1989, pp. 1173-1177, vol. 86.
Marko, M. A. et al., A Procedure for the Large-Scale Isolation of Highly Purified Plasmid DNA Using Alkaline Extraction and Binding to Glass Powder, Analytical Biochemistry 1982, pp. 382-387, vol. 121.
Melzak, Kathryn A. et al., Driving Forces for DNA Adsorption to Silica in Perchlorate Solutions, Journal of Colloid and Interface Science, 1996, pp. 635-644, vol. 181.
Polyakova, Yulia et al., Effect of Concentration of Ionic Liquid 1-Buytl-3-Methylimidazolium, Tetrafuoroborate, for Retention and Separation of Some Amino and Nucleic Acids, Journal of Liquid Chromatography & Related Technologies, 2006, pp. 1687-1701, vol. 29.
Stewart, Kent D. and Gray, Thomas A., Survey of the DNA Binding Properties of Natural and Synthetic Polyamino Compounds, Journal of Physical Organic Chemistry, 1992, pp. 461-466, vol. 5.
Uhlmann, Eugen and Peyman, Anusch, Antisense Oligonucleotides: A New Therapeutic Principle, Chemical Reviews, Jun. 1990, pp. 543-584, vol. 90, No. 4.
Volgelstein, Bert and Gillespie, David, Preparative and analytical purification of DNA from agarose, Proceedings of the National Academy of Sciences USA, Feb. 1979, pp. 615-619, vol. 76, No. 2.

(Continued)

*Primary Examiner* — Patrick Lewis

(57) ABSTRACT

Disclosed are water-soluble ionic liquids suitable for promoting adsorption of nucleic acids to a solid phase. The use thereof, particularly methods for the isolation of nucleic acids from an aqueous solution, as well as kits for performing those methods are disclosed.

3 Claims, 5 Drawing Sheets

OTHER PUBLICATIONS

Whelen, A. Christian and Persing, David H., The Role of Nucleic Acid Amplification and Detection in the Clinical Microbiology Laboratory, Annual Review of Microbiology, 1996, pp. 349-373, vol. 50.

Wu, Dan Y. and Wallace, R. Bruce, The Ligation Amplification Reaction (LAR)—Amplification of Specific DNA Sequences Using Sequential Rounds of Template-Dependent Ligation, Genomics, 1989, pp. 560-569, vol. 4.

* cited by examiner

A

B

C

D

ISOLATION AND PURIFICATION OF NUCLEIC ACIDS WITH A SOLID PHASE

RELATED APPLICATIONS

This application claims priority to European application EP 07008073.4 filed Apr. 20, 2007.

FIELD OF THE INVENTION

The present invention relates to the field of nucleic acid isolation and purification. A method and a kit for the isolation of nucleic acid from sample material are provided. In particular, the present invention is directed to methods and kits for obtaining a nucleic acid in a form that is substantially free from concomitant substances. The isolated nucleic acid is suitable for applications of molecular biology. The method of the invention includes adsorbing (i.e., reversibly binding) the nucleic acid to a solid phase, optionally washing the solid phase with the adsorbed nucleic acid, and eluting the nucleic acid from the solid phase.

BACKGROUND

Diagnostic tests and assays in the research field which are based on nucleic acid analysis are of still increasing importance. Since on the one hand, the nucleic acids are often present in very small concentrations and, on the other hand, they are often found in the presence of many other solid and dissolved substances, e.g., after lysis of cells or in sample material from food, they are difficult to isolate or to measure, in particular in biospecific assays which allow the detection of specific analytes. Therefore, in the majority of cases, these microbiological tests comprise at least one amplification step of the characteristic DNA molecules to be detected. A well-known assay which entails the selective binding of two oligonucleotide primers is the polymerase chain reaction (PCR) described in U.S. Pat. No. 4,683,195. This method allows the selective amplification of a specific nucleic acid region to detectable levels by a thermostable polymerase in the presence of deoxynucleotide triphosphates in several cycles. The PCR technology is a very sensitive technology with respect to both the required amount and the purity of the employed sample material.

Other possible amplification reactions are the ligase chain reaction (LCR, Wu, D., Y., and Wallace, R., B., Genomics 4 (1989) 560-569 and Barany, F., Proc. Natl. Acad. Sci. USA 88 (1991) 189-193); polymerase ligase chain reaction (Barany, F., PCR Methods and Appl. 1 (1991) 5-16); gap-LCR (PCT Patent Publication No. WO 90/01069); repair chain reaction (EP 0 439 182), 3SR (Kwoh, D., Y., et al., Proc. Natl. Acad. Sci. USA 86 (1989) 1173-1177; Guatelli, J., C., et al., Proc. Natl. Acad. Sci. USA 87 (1990) 1874-1878; PCT Patent Publication No. WO 92/0880A), and NASBA (U.S. Pat. No. 5,130,238). Further, there are strand displacement amplification (SDA), transcription mediated amplification (TMA), and $Q\beta$ amplification (for a review see e.g., Whelen, A., C. and Persing, D., H., Annu. Rev. Microbiol. 50 (1996) 349-373; Abramson, R., D. and Myers, T., W., Current Opinion in Biotechnology 4 (1993) 41-47).

As nucleic acids are only present within the cells of prokaryotic and eukaryotic organisms the cell wall has to be lysed prior to nucleic acid isolation. Concomitantly with the release of the nucleic acid from the cells, all other cellular components are also liberated. This includes proteins, salts, secondary metabolites as well as degradating enzyme, as e.g., proteases and nucleases. These enzymes start to degrade their target immediately. Thus the activity of these degrading enzymes has to be suppressed. This can be achieved by the addition of organic solvents or denaturating agents to the lysis solution. An alternative is the addition of protease and/or nuclease inhibitors.

In order to isolate nucleic acids from sample material there are several methods for the extraction of nucleic acids such as sequence-dependent or biospecific methods (e.g., affinity chromatography, hybridisation to immobilised probes) and sequence-independent or physico-chemical methods. Among the latter, well known to the art are liquid-liquid extraction with, e.g., phenol-chloroform, precipitation with an organic solvent such as ethanol, extraction with filter paper, extraction with micelle-forming agents such as cetyl-trimethyl-ammonium-bromide, interaction with immobilised, intercalating dyes such as acridine derivatives, as well as adsorption under chaotropic conditions to solid phases such as silica gel or diatomic earths, and adsorption to magnetic particles coated with, e.g., glass or magnetic organo silane particles.

Frequently, cationic surfaces are used to isolate nucleic acids. Such surfaces may be used to adsorb charged DNA molecules, whereby, e.g., EP 0 281 390 describes a polycationic support for nucleic acid isolation, WO 01/94573 charged membranes or WO 00/69872 a pH dependent ion exchange matrix. WO 02/48164 discloses polymers with switchable charge on solid supports for reversible binding of DNA. Similar to cationic surfaces, polycationic entities have certain DNA-binding affinity, too. Stewart, K., D., et al., J. Phys. Org. Chem. 5 (1992) 461-466 reports an increasing affinity of polyamines in solution for binding to DNA with increasing cationic charge. Doré, K., et al, J. Am. Chem. Soc. 126 (2004) 4240-4244 describes the selectivity of cationic compounds between double-stranded and single-stranded nucleic acids.

Another approach, normally applied to the separation and isolation of, e.g., DNA from complex biological fluids, is the use of nucleic acid binding materials. For example, the most prominent example of DNA binding material are glass surfaces due to their ability to reversibly bind DNA in the presence of chaotropic reagents and/or alcoholic additives (Vogelstein, B., and Gillespie, D., Proc. Natl. Acad. Sci. USA 76 (1979) 615-619). Such binding is assumed to be effected by oxidic surfaces ("X—OH") interacting with phosphate groups of the nucleic acids.

A common method for the isolation of nucleic acids was published 1987 by Chomczynski, P., and Sacchi, N., Anal. Biochem. 162 (1987) 156-159. This method exploits the different solubilities of proteins and nucleic acids for an extractive separation protocol with an acidic guanidinium thiocyanate—phenol/chloroform mixture.

Boom, R., et al., J. Clin. Microbiol. 28 (1990) 495-503 describes a small scale protocol for the purification of DNA and RNA from sample material. The method is based on the lysing and nuclease-inactivating properties of a chaotropic agent in the presence of an EDTA/detergent mixture and the nucleic acid-binding properties of silica particles.

Lithium salts of nucleic acids are known to have a reduced solubility in aqueous solutions. In the European Patent Application EP 0 818 461 a method for the isolation of ribonucleic acid with an acidic solution containing a lithium salt and a chaotropic agent as well as an nucleic acid-binding partner such as silica particles is described.

In the U.S. Pat. No. 5,808,041 a composition for isolating nucleic acids from cells is described. The compositions are mixtures of silica gel and glass particles combined with chaotropic salts.

In WO 99/61603 a method for separating and/or isolating circular nucleic acids under alkaline conditions at a pH>8 with a solid matrix consisting essentially of a silica material in presence of at least one chaotropic substance is described.

US patent application 2004/0121336 describes a method of binding a predetermined amount of a nucleic acid to a multiplicity of solid substrate binding units. A method for gently lysing and solubilizing cells is described in US patent application 2004/0180445.

In view of certain disadvantages of the state of the art, it is the objective of the current invention to provide an alternative method for the isolation and purification of nucleic acid molecules from complex sample material. A particular object of the invention is to provide alternative compounds to promote the adsorption of a nucleic acid to a solid substrate.

SUMMARY OF THE INVENTION

Therefore the subject matter of the present invention is to provide further compositions and methods to adsorb a nucleic acid to a solid phase. The particular use of such compositions and methods is the isolation and purification of nucleic acid molecules. The inventors surprisingly found that a nucleic acid can be adsorbed to a solid phase in the presence of a water-soluble ionic liquid.

Therefore, a first aspect of the invention is a liquid composition for adsorbing a nucleic acid to a solid phase, characterized in that the composition comprises (a) a salt which is a liquid at room temperature (ionic liquid) and which comprises an organic cation of Formula I

whereby Y is selected from the group consisting of a carbon atom and a nitrogen atom, whereby X is selected from the group consisting of a hydrogen atom, a carbon atom and a nitrogen atom, and whereby a delocalized positive charge extends over Y and N, or all components of the functional group; and (b) an aqueous buffer.

A further aspect of the invention is the use of a water-soluble ionic liquid comprising an organic cation of Formula I, whereby Y is selected from the group consisting of a carbon atom and a nitrogen atom, whereby X is selected from the group consisting of a hydrogen atom, a carbon atom and a nitrogen atom, and whereby a delocalized positive charge extends over Y and N, or all components of the functional group; for adsorbing a nucleic acid to a solid phase.

A further aspect of the invention is a method to enhance the effect of a chaotropic compound on the interaction of a nucleic acid and a solid phase, whereby the nucleic acid is present in a solution comprising an aqueous buffer and a chaotropic agent, characterized in that an effective amount of an ionic liquid is added to the adsorption solution, whereby the ionic liquid comprises an organic cation of Formula I, whereby Y is selected from the group consisting of a carbon atom and a nitrogen atom, whereby X is selected from the group consisting of a hydrogen atom, a carbon atom and a nitrogen atom, and whereby a delocalized positive charge extends over Y and N, or all components of the functional group, and whereby the ionic liquid enhances adsorption of the nucleic acid to a solid phase.

A further aspect of the invention is a method for isolating a nucleic acid, comprising the following steps (a) providing the following components: (i) a solid phase capable of reversibly binding nucleic acids; (ii) sample material containing the nucleic acid; (iii) a solution containing an ionic liquid comprising an organic cation of Formula I whereby Y is selected from the group consisting of a carbon atom and a nitrogen atom, whereby X is selected from the group consisting of a hydrogen atom, a carbon atom and a nitrogen atom, and whereby a delocalized positive charge extends over Y and N, or all components of the functional group; (iv) an aqueous buffer; (b) contacting the provided components under conditions suitable for adsorbing the nucleic acid to the solid phase; (c) separating the solid phase with the adsorbed nucleic acid from the solution; (d) eluting the nucleic acid from the solid phase.

A further aspect of the invention is a method for adsorbing RNA to a solid phase, characterized in that the method comprises (a) providing the following components: (i) a solid phase capable of reversibly binding nucleic acids; (ii) a sample material containing the ribonucleic acid; (iii) an aqueous solution containing a butylmethylimidazolium cation at a concentration from 1 M to 3 M; and (b) contacting the provided components under conditions suitable for adsorbing the ribonucleic acid to the solid phase.

A further aspect of the invention is a kit for isolating nucleic acid from nucleic acid containing material, characterized in that the kit comprises (a) a solid phase capable of reversibly binding nucleic acids; (b) an ionic liquid comprising an organic cation of Formula I, whereby Y is selected from the group consisting of a carbon atom and a nitrogen atom, whereby X is selected from the group consisting of a hydrogen atom, a carbon atom and a nitrogen atom, and whereby a delocalized positive charge extends over Y and N, or all components of the functional group.

DETAILED DESCRIPTION OF THE INVENTION

The present invention provides new compositions and methods for the purification of nucleic acids. Certain terms are used with particular meaning, or are defined for the first time, in this description of the present invention. For the purposes of the present invention, the terms used are defined by their art-accepted definitions, when such exist, except that when those definitions conflict or partially conflict with the definitions set forth below. In the event of a conflict in definition, the meaning of a terms is first defined by any of the definitions set forth below.

The term "comprising" is used in the description of the invention and in the claims to mean "including, but not necessarily limited to".

The articles "a" and "an" are used herein to refer to one or to more than one (i.e., to at least one) of the grammatical object of the article. By way of example, "a compound" means one compound or more than one compound.

When designating a range of numerical values such as a concentration range, the range is indicated by the word "between", followed by a first value n1 and a second value n2. The lower boundary of the designated range is understood as being the value equal to or higher than the first value. The higher boundary of the designated range is understood as being the value equal to or lower than the second value". Thus, a value x the designated range is given by $n1 \leq x \leq n2$.

Further, it is understood that the term "about" in combination with a numerical value n indicates a value x in the interval given by the numerical value ±5% of the value, i.e., $n-0.05*n \leq x \leq n+0.05*n$. In case the term "about" in combination with a numerical value n describes a preferred embodiment of the invention, the value of n is most preferred, if not indicated otherwise.

The term "solid phase" to which a nucleic acid is adsorbed is understood as being a substrate which is insoluble in the compositions according to the invention. A preferred solid phase is a substrate with a surface capable of interacting with the phosphate groups of the backbone of nucleic acids. The solid phase may be in the form of porous or non-porous particles, powdered particles, or fibers. A solid phase consisting of fleece material which comprises a plurality of non-woven fibers is also encompassed. Preferred solid phases consist of glass. Preferred solid phases are porous or non-porous mineral substrates such as silica, quartz, celites or other materials with oxidic surfaces (including, e.g., zirconium oxide, aluminum oxide, and other metal oxides) or mixtures thereof. Also, the term "solid phase" encompasses magnetically attractable particles coated with silica, glass, quartz, or celites. Further, it is understood that a substrate in the form of "powder" or "powdered" material refers to finely divided material which, when dispersed in a liquid composition according to the invention, produces a suspension. The term "powder" or "powdered" material is intended to include tablets, in which the powdered material has been aggregated, but still yields a suspension when combined with a liquid phase.

The term "silica" as used within this application denotes materials which are mainly build up of silicon and oxygen. These materials comprise silica, silicon dioxide, silica gel, fumed silica gel, diatomaceous earth, celite, talc, quartz, glass, glass particles including all different shapes of these materials. Glass particles, for example, may comprise particles of crystalline silica, soda-lime glasses, borosilicate glasses, and fibrous, non-woven glass.

The term "magnetic particle" denotes a particle with paramagnetic or superparamagnetic properties. That is to say, the particle is magnetically displaceable but does not retain any magnetisation in the absence of an externally applied magnetic field.

The term "sample" (or "sample material") as used herein refers to a complex sample, more preferred a biological sample. A complex sample may contain a plurality of organic and inorganic compounds which are desired to be separated, from the nucleic acid. The term "sample" also encompasses an aqueous solution containing nucleic acids derived from other origins, e.g., from chemical or enzymatic reaction mixtures, or from a previous purification of biological sample material. The term biological sample, from which nucleic acids are purified, encompasses samples comprising viruses or bacterial cells, as well as isolated cells from multicellular organisms such as human and animal cells as well as tissues and cell cultures. Particularly, the sample can contain leucocytes, and other immunologically active cells, chemical compounds with a low and/or a high molecular weight such as haptens, antigens, antibodies and nucleic acids. The sample can be whole blood, blood serum, blood plasma, cerebral fluid, sputum, stool, biopsy specimens, bone marrow, oral rinses, tissues, urine or mixtures thereof. The present invention also encompasses biological samples such as a fluid from the human or animal body; preferably the biological sample is blood, blood plasma, blood serum or urine. The blood plasma is preferably EDTA, heparin or citrate blood plasma. In an embodiment of the invention the biological sample comprises bacterial cells, eukaryotic cells, viruses or mixtures thereof. A biological sample as exemplified above, preferably in a processed form such as a lysate, can be part of the composition from which the (target) nucleic acid is adsorbed to the substrate. Also encompassed by the term "biological sample" are cells from plants, and fungi as well as single cell organisms.

A preferred sample according to the invention is a lysate. A "lysate" or a "lysed sample" can be obtained from a complex sample and/or biological sample material comprising tissue, cells, bacteria or viruses, whereby the structural integrity of the material is disrupted. To release the contents of cells, tissue or, more generally, from the particles which make up a biological sample, the material may be treated with enzymes or with chemicals to dissolve, degrade or denature the cellular walls and cellular membranes of such organisms. This process is encompassed by the term "lysis". It is common to use chaotropic agents such as a guanidine salt and/or anionic cationic, zwitterionic or non-ionic detergent when nucleic acids are set free in the lysis process. It is also an advantage to use proteases which rapidly degrade enzymes with nucleolytic activity and other unwanted proteins. In case there remains particulate, i.e., undissolved matter of the sample material following the lysis process, the particulate matter is usually separated from the lysate to result in a cleared lysate. This can be done, e.g., by way of filtering or centrifugation. In such a case the cleared lysate is processed further, e.g., by a method according to the invention. Thus, the term "lysed sample" encompasses a cleared lysate.

A "chaotropic agent" according to the present invention is any chemical substance which disturbs the ordered structure of liquid water. A chaotropic agent also facilitates unfolding, extension and dissociation of proteins (Dandliker, W., B., and de Saussure, V., A., In: The Chemistry of Biosurfaces, Hair, M., L., ed., Marcel Dekker, Inc. New York (1971) p. 18). Preferred chaotropic salts are sodium iodide, sodium perchlorate, guanidinium thiocyanate, guanidinium isothiocyanate or guanidinium hydrochloride. Another preferred chaotropic agent is urea.

The terms "aqueous", "aqueous" phase and "aqueous" solution describe a liquid phase of which the solvent portion comprises water. However, other solvents such as a water-miscible organic solvent can be present in the solvent portion, too. In view of the presence of other solvents a solution is considered "aqueous" when between 30% and 100%, measured as volume by volume [v/v], of the solvent portion is water.

The term "nucleic acid" as used within this application denotes DNA and RNA polynucleotides of natural and synthetic origin. This includes modified nucleotides as e.g., dideoxyribonucleotides, nucleobases with modified sugar residues and nucleobases with modified base moieties (see e.g., Scheit, K., H., Nucleotide Analogs, John Wiley and Sons, N.Y. (1980); Uhlmann, E., and Peyman, A., Chem. Rev. 90 (1990) 543-584). In particular genomic DNA, complementary DNA (cDNA), messenger RNA (mRNA), transfer RNA (tRNA), ribosomal RNA (rRNA) and micro RNA (miRNA) is included.

An "ionic liquid" is a liquid that contains only ions. In the broad sense, this term includes all the molten salts, for instance, sodium chloride at temperatures higher than 800° C. However, in this document the term "ionic liquid" is used for salts whose melting point is relatively low. In the context of the present invention the term "ionic liquid" means a salt that is a liquid at room temperature. In addition, the ionic liquid according to the invention is a water-soluble ionic liquid. The "ionic liquid" at the same time denotes a salt composed of a cation and an anion. The anion can be an anorganic or organic anion, the cation is mostly an organic cation, but in any case one ion (anion or cation) is an organic ion. The cation may comprise imidazolium cations, pyridinium cations, ammonium cations, phosphonium cations and substituted guanidinium cations. At least one ion of the ion pair has a delocalized charge. Due to the weak interactions between both ions, these ionic liquids display a low melting point.

The term "adsorption"/"adsorbing" generally means adhere or attach molecules or ions (the "solute") to outer surfaces or interfaces so as to increase the concentration of a solute in the vicinity of a solid surface, over that in the bulk of the solution, due to the attractive interaction between the solid immersed into the solution and the solute. The binding to the surface is usually weak and reversible. It is a surface process such that the accumulating molecules do not actually penetrate the substance on which they are formed. The term is not to be confused with absorption which means the filling of pores in a solid.

The isolation and purification of nucleic acids is often linked with the use of chaotropic agents like guanidinium salts in high concentrations for adsorbing the nucleic acids to solid phases such as silica matrices (Vogelstein, B., and Gillespie, D., Proc. Natl. Acad. Sci. USA 76 (1979) 615-619; Marko, M., A., et al., Anal. Biochem. 121 (1982) 382-387).

Examples for chaotropic salts are guanidinium salts such as guanidinium thiocyanate, guanidinium isothiocyanate or guanidinium hydrochloride but also sodium iodide, sodium perchlorate. Other compounds known to the skilled artisan are also possible. A chaotropic substance effects removal of water molecules from the hydrate shell of dissolved nucleic acid molecules as well as from the surface of the solid phase, e.g., a silica matrix. As a result, a direct ionic interaction between the —Si—OH groups of the silica matrix and the phosphate-di-ester groups of the nucleic acid backbone becomes possible in this particular case (Melzak, K., A., et al., J. Coll. Interf. Sci. 181 (1996) 635-644).

The described chaotropic effect is accompanied by an increase of the entropy. Thus, the equilibrium is shifted to the binding of the nucleic acid to the surface of the solid phase. As a prerequisite, the surface of the solid phase has to be in a neutral state. Especially for the surface of a silica material, the preferred pH range for adsorbing the nucleic acid is between pH 4 and pH 6. Additives, e.g., other elements as boron, iron, phosphor, aluminum and the like, present in the silica matrix may shift the appropriate conditions. The chaotropic effect can be enhanced by the addition of other dehydrating substances. For example, addition of an organic solvent, e.g., an alcohol, results in an improved adsorption of nucleic acids to glass surfaces.

The inventors surprisingly found that certain ionic liquids have an effect which is similar to the effect of chaotropic agents. The inventors could show that certain ionic liquids efficiently promote the adsorption of nucleic acids from an aequous solution to a solid phase. A first aspect of the current invention therefore is a liquid composition for adsorbing a nucleic acid to a solid phase, characterized in that the composition comprises (a) an ionic liquid comprising an organic cation of Formula I

whereby Y is selected from the group consisting of a carbon atom and a nitrogen atom, whereby X is selected from the group consisting of a hydrogen atom, a carbon atom and a nitrogen atom, and whereby a delocalized positive charge extends over Y and N, or all components of the functional group; and (b) an aqueous buffer. Another embodiment of the invention is the use of an ionic liquid comprising an organic cation of Formula I and as defined above for adsorbing a nucleic acid to a solid phase. The composition according to the invention which additionally contains a nucleic acid is also referred to as an "adsorption solution" because the composition provides conditions necessary for adsorbing the nucleic acid to a solid phase.

Preferably, Y and X are nitrogen atoms and the delocalized positive charge extends over the components Y, X, and N of Formula I. Thus, the core of the ionic liquid can be a guanidinium residue which carries a positive charge of the cation. At least one of the components Y, N, and X additionally carries a further substituent. A preferred substituent is selected from the group consisting of a halogen-, an alkyl-, a hydroxyalkyl-, an alkoxyalkyl- and a phenoxyalkyl-function. Highly preferred, the cation of the ionic liquid is selected from the group consisting of N-(1-butyl)-guanidinium, N-1-(2-methoxyethyl)-guanidinium, and n-butane-1,4-diguanidinium. The skilled person readily appreciates that in the case of the latter diguanidinium compound a positive charge can be present on either guanidinium group or on both.

Alternatively and with great advantage, X is a carbon atom, Y is a nitrogen atom, Y and N are part of a cyclic system with conjugated double bonds and the delocalized charge extends over Y and N. Examples for ionic liquids with such a core are compounds with a pyridinium or an imidazolium moiety. Particular examples therefor are benzimidazolium moieties. Also in this case at least one of the components Y, N, and X additionally carries a further substituent. A preferred substituent is selected from the group consisting of an alkyl-, a hydroxyalkyl-, an alkoxyalkyl- and a phenoxyalkyl-function. Highly preferred, the cation of the ionic liquid is selected from the group consisting of 1-ethyl-3-methyl imidazolium, 1-butyl-3-methyl-imidazolium, 3-methyl-1-[4-(3-methyl-3H-benzimidazol-1-ium)-but-1-yl]-3H-benzimidazolium-di (toluoylsulfat), and 1-butyl-pyridinium.

Ionic liquids according to the invention are capable of promoting the adsorption of a nucleic acid to a solid phase, preferably a solid phase with a silica surface, and preferably under acidic conditions without the further need of a chaotropic substance such as a guanidinium salt (e.g., guanidinium hydrochloride, guanidinium thiocyanate, guanidinium isothiocyanate). However, while not absolutely required, a chaotropic substance can be of great advantage in further promoting adsorption. It was surprisingly found that adsorption of a nucleic acid to a solid phase can be enhanced by the addition of a compound comprising a butylmethylimidazolium cation to an adsorption solution comprising a conventional chaotropic agent (e.g., Example 2, experiment No. 5, also see FIG. 1). Thus, a further embodiment of the invention is a method to enhance the effect of a chaotropic compound on the interaction of a nucleic acid and a solid phase, whereby the nucleic acid is present in a solution comprising an aqueous buffer and a chaotropic agent, characterized in that an effective amount of an ionic liquid is added to the adsorption solution, whereby the ionic liquid comprises an organic cation of Formula I, whereby Y is selected from the group consisting of a carbon atom and a nitrogen atom, whereby X is selected from the group consisting of a hydrogen atom, a carbon atom and a nitrogen atom, and whereby a delocalized positive charge extends over Y and N, or all components of the functional group, and whereby the ionic liquid enhances adsorption of the nucleic acid to a solid phase.

It is therefore preferred that the composition additionally contains a chaotropic substance. More preferred, the chaotropic substance is a guanidinium salt. Preferred guanidinium salts are guanidinium hydrochloride (guanidinium HCl, Gu-HCl), guanidinium thiocyanate, and guanidinium isothiocyanate.

A further effect of chaotropic agents is the inhibition of nucleic acid degrading enzymes present during the isolation of the nucleic acid. Additionally reducing agents like dithiotreitol (DTT) may be added. For cell lysis detergents are added, e.g., 20% (w/w) of Triton X-100. The detergent also has an influence on the binding characteristics of nucleic acids to the solid phase. The agents used for adsorbing nucleic acids to a solid phase need to provide good and selective binding conditions. To improve the selectivity of the interaction with the solid phase concomitant polypeptides and proteins have to be removed. This can be done for example by an enzymatic digestion with proteinase K. However, some proteolytic enzymes do not work properly at high concentrations of chaotropic agents.

In an experiment the binding of herring sperm DNA in the presence of different combinations of a chaotropic agent, an alcohol and a detergent was examined. Herring sperm DNA is composed of high and low molecular weight DNA. The surprising result for binding of herring sperm DNA to glass fleece is shown in FIG. 1. It can be seen that the amount of bound DNA varies, depending on the conditions for adsorption and the ionic liquid used. Very good adsorption to the solid phase (two different silica matrices were used) was achieved using 3 M butylmethylimidazolium at pH 4.5.

Generally, the preferred solid phase to which the nucleic acid is adsorbed using the compositions and methods according to the invention comprises a porous or non-porous solid substrate. Very much preferred is a silica substrate. More preferred, the silica substrate is selected from the group consisting of silica gel, glass fibers, quartz fibers, and celites. Also preferred, the solid phase comprises a porous or non-porous mineral substrate selected from the group consisting of metal oxides, and/or metal mixed oxides, alumina, titania, zirconia, and materials predominantly consisting of glass.

It is also preferred that the solid phase has a particle size of 0.1 µm to 100 µm. It is also preferred that porous solid phase materials, when employed, have a pore size of from 2 to 1,000 nm. More preferred, porous or non-porous solid phase materials, especially celites, are in the form of loose packings. Even more preferred, the solid phase consists of filter sheets in the form of glass, quartz or ceramic filter sheets, and/or a membrane containing silica gel and/or particles or fibers of mineral substrates and fabrics of quartz or glass wool, that is to say fibrous, non-woven glass.

It is also preferred that the solid phase comprises magnetically attractable particles. More preferred, the magnetically attractable particles are coated with a mineral substrate selected from the group consisting of silica, glass, quartz, and celites. Even more preferred, the substrate comprises magnetically attractable particles coated with glass. The magnetic glass particles used in the present invention may be provided in different formulations. It is possible to provide them in the form of a tablet, as a powder or as a suspension. Very much preferred, the magnetic glass particles are suspended in a liquid composition according to the invention. Preferably, these suspensions contain between 5 to 100 mg/ml magnetic glass particles (MGPs). Also preferred, the silica-containing material is suspended in aqueous buffered solutions which may optionally contain an ionic liquid according to the invention.

It has further been found that the inclusion of certain additives in the compositions according to the invention further increase the adsorption of a nucleic acid from an aqueous solution to the solid phase. It is preferred that the composition of the invention additionally contains a compound selected from the group consisting of magnesium(II)chloride, and imidazole.

The procedure of adsorbing a (at least one) nucleic acid to a substrate such as, e.g., glass particles can be described as follows. According to the invention, the method for adsorbing a nucleic acid to the solid phase comprises the steps of (a) providing the following components: (i) a solid phase capable of reversibly binding nucleic acids; (ii) sample material containing the nucleic acid; (iii) a composition according to the invention; and (b) contacting the provided components under conditions suitable for adsorbing the nucleic acid to the solid phase.

The sample material is preferably homogenized in the composition of step (iii) when step (b) is performed. The sample material may comprise biological material. In this case, a homogenization step is performed before step (b). If necessary, after homogenization residual particulate matter such as cell debris is separated from the remaining homogenized sample material by centrifugation and the supernatant is further processed by executing step (b). Alternative separation techniques are known, apart from centrifugation, including filtration.

According to the invention, the procedure of adsorbing the nucleic acid is performed in the presence of an ionic liquid comprising an organic cation of Formula I, whereby Y is selected from the group consisting of a carbon atom and a nitrogen atom, whereby X is selected from the group consisting of a hydrogen atom, a carbon atom and a nitrogen atom, and whereby a delocalized positive charge extends over Y and N, or all components of the functional group. Very much preferred, the cation of the ionic liquid is selected from the group consisting of N-(1-butyl)-guanidinium, N-1-(2-methoxyethyl)-guanidinium, n-butane-1,4-diguanidinium, 1-ethyl-3-methyl imidazolium, 1-butyl-3-methyl-imidazolium, 3-methyl-1-[4-(3-methyl-3H-benzimidazol-1-ium)-but-1-yl]-3H-benzimidazolium-di(toluoylsulfat), and 1-butyl-pyridinium.

It is preferred that the concentration of the ionic liquid in the composition according to the invention is in the range between 0.02 M and 4 M. More preferred, the concentration is between 0.03 M and 3 M.

It is also preferred that contacting the solid phase with the nucleic acid in the presence of a composition according to the invention is performed in a pH range between pH 4.0 and pH 8.0. Acidic conditions are more preferred. This means that in this more preferred embodiment the adsoption process takes place at a pH below 7 and above 4, preferably between pH 4.5 and pH 6.5, most preferred at pH 6. It is obvious for the skilled person to produce suitable aqueous buffered solutions. Buffer systems which suitable for molecular biology purposes may be found e.g., in Sambrook, J., et al., Molecular Cloning, A Laboratory Manual, 3rd edition, CSHL Press (2001) Cold Spring Harbor, N.Y. Preferred buffer substances are Tris-(hydroxymethyl)-aminomethane (TRIS), 2-morpholinoethanesulfonic acid (MES) phosphate, N-(2-Hydroxyethyl) piperazine-N'-(2-ethanesulfonic acid) (HEPES), acetate, salts thereof, and other suitable substances.

The purification effect results from the behavior of DNA or RNA to bind to material of the solid phase under these conditions, i.e., in the presence of the compositions according to the invention. To bring the sample in contact with the substrate, i.e., the material with an affinity to nucleic acids, the sample is mixed with the material and incubated for a period of time sufficient for the binding to occur. Experts are usually familiar with the duration of the incubation step from procedures for performing comparable treatment of solid phases in the presence of, e.g., an alcohol and a chaotropic salt as described in the state of the art. This step can be optimized by determining the quantity of immobilized nucleic acid on the surface of the solid phase at different points in time. Incubation times of between 10 seconds and 30 minutes can be appropriate for nucleic acids. After incubation, the adsorbed target component is separated from the liquid phase. This may be achieved in general by gravity.

In the convenient case of nucleic acids bound to magnetic glass particles the separation step is performed by way of applying a magnetic field to the magnetic particles with the adsorbed nucleic acid material. For instance, the magnetic particles can be pulled to the wall of the vessel in which incubation was performed. The liquid containing the sample contents that are not bound to the magnetic particles can then be removed. The removal procedure used depends on the type of vessel in which incubation was performed. Suitable steps include removing the liquid via pipetting or aspiration.

Another preferred way is the use of so-called "spin columns" or "spin filter columns" which are commercially available such as as HIGH PURE (Roche Diagnostics Operations, Inc.) columns from Roche Diagnostics GmbH Mannheim, Germany. Spin filter column tubes usually contain a fleece of non-woven glass fibers located at the bottom of the column and covering the opening at the bottom. The adsorption solution containing the nucleic acid is transferred to the column and passed through the fleece by applying force. The term "force" includes gravitational force and, preferred, centrifugal force. Very much preferred is the "spin column" procedure wherein the adsorption solution is passed through the filter due to force being applied by way of centrifugation. Other ways to pass the adsorption solution through the fleece include the application of pressure or suction.

The solid phase with the adsorbed nucleic acid may then be washed at least once with a wash solution. The washing step or steps is optional. A wash solution is used that does not cause the target component to be released from the material surface but that washes away the undesired contaminants as thoroughly as possible. This wash step preferably takes place by incubating the material with the bound target nucleic acid(s) with the wash solution. The material is preferably resuspended during this step. Also preferred, in case the material is a glass fleece or a packing in a column, the washing step takes place by rinsing the column with the washing solution. Preferably, the washing solution is passed through the column by applying pressure, suction, centrifugal force or gravitational force. Suitable wash solutions are known to the skilled person and may contain a salt, a chaotropic substance and/or an organic solvent such as an alcohol. The contaminated wash solution is preferably removed just as in the step described above for adsorbing the nucleic acid to the solid phase. After the last washing step, the separated material of the solid phase with the adsorbed nucleic acids can be dried briefly in a vacuum, or the fluid can be allowed to evaporate. A pretreatment step using acetone may also be performed.

Afterwards, the conditions are changed to release the nucleic acid from the solid phase. This step is also referred to as "eluting" the nucleic acid. The solid phase with the immobilized biological material is contacted with an aequous solution with no or only a low amount of chaotropic agent and/or organic solvent and/or ionic liquid. Alternatively, the suspension can be diluted with a solution with no or only a low amount of chaotropic agent and/or organic solvent and/or ionic liquid. Buffers of this nature are known to the skilled person, e.g., from DE 37 24 442 and Jakobi, R., et al., Anal. Biochem. 175 (1988) 196-201. The elution buffers with a low salt content are in particular buffers with a content of less than 0.2 mol/l. Preferably, the elution buffer contains the substance Tris for buffering purposes. Also preferred, the elution buffer is demineralized water. The solution containing the purified nucleic acid can now be used for other reactions. Optionally, the nucleic acid(s) can be precipitated from the solution using, e.g., ethanol or isopropanol. The precipitate can also be subjected to further washing steps. Methods of this kind are well known to the skilled artisan and are described in detail in Sambrook, J., et al., Molecular Cloning, A Laboratory Manual, 3rd edition, CSHL Press (2001) Cold Spring Harbor, N.Y.

Yet, another aspect of the invention is a method for isolating a nucleic acid, comprising the following steps (a) providing the following components: (i) a solid phase capable of reversibly binding nucleic acids; (ii) sample material containing the nucleic acid; (iii) a solution containing an ionic liquid comprising an organic cation of Formula I whereby Y is selected from the group consisting of a carbon atom and a nitrogen atom, whereby X is selected from the group consisting of a hydrogen atom, a carbon atom and a nitrogen atom, and whereby a delocalized positive charge extends over Y and N, or all components of the functional group; (iv) an aqueous buffer; (b) contacting the provided components under conditions suitable for adsorbing the nucleic acid to the solid phase; (c) separating the solid phase with the adsorbed nucleic acid from the solution; (d) eluting the nucleic acid from the solid phase. In a preferred embodiment of the invention, the nucleic acid is DNA and RNA. In another preferred embodiment, the nucleic acid is DNA. In yet another preferred embodiment, the nucleic acid is RNA. Very much preferred, step (b) is performed under acidic conditions. Even more preferred, step (b) is performed at a pH between 4 and 6.5. Yet, even more preferred, step (b) is performed at a pH between 4.5 and 6.

It was further surprisingly found that the binding of RNA to silica matrices can be controlled depending on the concentration of the butylmethylimidazolium cation. This is shown in FIG. 4 for yeast RNA. At low butylmethylimidazolium concentrations, i.e., at 1-2M, only low amounts of yeast RNA are adsorbed to the silica matrices. At elevated concentrations, such as 3 M butylmethylimidazolium, the adsorption of yeast RNA to the silica matrix is enhanced.

Another embodiment of the invention is the use of butylmethylimidazolium tetrafluoroborate for adsorbing RNA to a solid phase, characterized in that the concentration of the ionic liquid is from 1 M to 3M. It has been found that this concentration range is especially suited to promote the adsorption of RNA to the solid phase, whereas at lower concentrations RNA is bound to a lesser extent (see FIG. 4). Thus, a very much preferred embodiment of the invention, is a method for adsorbing RNA to a solid phase, characterized in that the method comprises (a) providing the following components: (i) a solid phase capable of reversibly binding nucleic acids; (ii) a sample material containing the ribonucleic acid; (iii) a solution containing a butylmethylimidazolium cation at a concentration from 1 M to 3 M; and (b) contacting the provided components under conditions suitable for adsorbing the ribonucleic acid to the solid phase. Very much preferred, step (b) is performed under acidic conditions. Even more preferred, step (b) is performed from pH 4 to pH 6.5. Yet, even more preferred, step (b) is performed from pH 4.5 to pH 6. Most preferred, step (b) is performed at pH 6.

The invention also contemplates kits. Such kits known to the art comprise plasticware useful in the sample preparation procedure. Examples therefor are microwell plates in the 96 or 384 well format or just ordinary reaction tubes manufactured e.g., by Eppendorf, Hamburg, Germany. The kits of the invention also comprise some or all other reagents for carrying out the methods according to the invention. Therefore, a kit can additionally contain a solid phase, i.e., a material with an affinity to nucleic acids. Preferably the solid phase comprises a material with a silica surface. Very much preferred, the solid phase comprises glass or quartz fibers. Also very much preferred, the solid phase is a composition comprising magnetic glass particles, i.e., magnetically attractable particles coated with glass. The kit can further or additionally comprise a lysis buffer containing e.g., a chaotropic agent, a detergent or mixtures thereof. These components of the kit according to the invention may be provided separately in tubes or storage containers. Depending on the nature of the components, these may be even provided in a single tube or storage container. The kit may further or additionally comprise a washing solution which is suitable for the washing step of the solid phase where DNA or RNA or both are bound thereto. This washing solution may contain an ionic liquid according to the invention and/or a chaotropic agent in a buffered solution or solutions with an acidic pH. Often the washing solution or other solutions are provided as stock solutions which have to be diluted before use. The kit may further or additionally comprise a desorption solution, i.e., an elution buffer, that is to say a solution for desorbing the nucleic acid from the solid phase. A preferred desorption solution can be a buffer (e.g., 10 mM Tris, 1 mM EDTA, pH 8.0) or pure water. Further, additional reagents or buffered solutions may be present which can be used for the purification process of a nucleic acid, i.e., DNA or RNA. Thus, another aspect of the invention is a kit for isolating nucleic acid from nucleic acid containing material, characterized in that the kit comprises (a) a solid phase capable of reversibly binding nucleic acids; (b) an ionic liquid comprising an organic cation of Formula I, whereby Y is selected from the group consisting of a carbon atom and a nitrogen atom, whereby X is selected from the group consisting of a hydrogen atom, a carbon atom and a nitrogen atom, and whereby a delocalized positive charge extends over Y and N, or all components of the functional group.

It was also surprisingly found that the addition of magnesium(II) chloride and imidazole also can improve the nucleic acid binding mediated by guanidinium such as guanidinium hydrochloride. A particular advantage of imidazole as binding enhancer is that it can be used at the same time as buffer salt for adjusting the pH value of the sample solution. Therefore, a further aspect of the invention is a liquid composition for adsorbing a nucleic acid to a solid phase, characterized in that the composition comprises (a) a guanidinium salt and/or an ionic liquid comprising an organic cation of Formula I, whereby Y is selected from the group consisting of a carbon atom and a nitrogen atom, whereby X is selected from the group consisting of a hydrogen atom, a carbon atom and a nitrogen atom, and (b) a compound selected from the group consisting of magnesium(II)chloride, and imidazole. The invention also comprises the use of magnesium(II) chloride for adsorbing a nucleic acid to a solid phase from an adsorption solution which comprises the nucleic acid. The invention further comprises the use of imidazole for adsorbing a nucleic acid to a solid phase from an adsorption solution which comprises the nucleic acid. In addition, the present invention comprises a method for isolating a nucleic acid, characterized in that said method comprises the following steps (a) providing the following components: (i) a solid phase capable of reversibly binding nucleic acids; (ii) sample material containing the nucleic acid; (iii) an adsorption solution containing a compound selected from the group consisting of magnesium (II) chloride, and imidazole; (b) contacting the provided components under conditions suitable for adsorbing the nucleic acid to the solid phase; (c) separating the solid phase with the adsorbed nucleic acid from the solution; (d) eluting the nucleic acid from the solid phase.

The following examples, references, and figures are provided to aid the understanding of the present invention, the true scope of which is set forth in the appended claims. It is understood that modifications can be made in the procedures set forth without departing from the spirit of the invention.

SPECIFIC EMBODIMENTS

Example 1

Comparison of the Binding of Different Nucleic Acid Samples Under Different Conditions Herring sperm DNA (Roche Applied Science, Roche Diagnostics GmbH Mannheim, Cat. No. 10223646) was used in each experiment at a concentration of 120 µg DNA/500 µl.

Calf thymus DNA (Roche Applied Science, Roche Diagnostics GmbH Mannheim, Id No. 10041785) was used either at 50 µg or 100 µg DNA/500 µl.

RNA isolated from baker's yeast using conventional techniques was used in each experiment at a concentration of 79 µg RNA/500 µl.

Spin filter columns, e.g., HIGH PURE columns (e.g., from Roche Applied Science, Cat. No. 11796828; Roche Diagnostics GmbH Mannheim) either contained type A or type B glass fleece DNA or RNA was dissolved in aqueous buffers as indicated in Examples 2 to 5, and 500 µl of the respective solution was loaded on a spin column. Each column was attached to a sample tube. After centrifugation on a microcentrifuge [Eppendorf 5415 C] at 8,000 r.p.m for 1 min a sample was taken from each flow-through. Following a 1:5 dilution with water the nucleic acid concentration was determined by measuring the difference of the extinction at 260 nm wavelength. As a control, the same measurement was performed with the correspondig "loading solution", that is the nucleic acid solution which was loaded on the spin column. The concentration difference before and after loading was determined as a quantitative measure for the nucleic acid bound to the respective solid phase.

Example 2

Adsorption of Herring Sperm DNA to Glass Fleece of Two Different Spin Columns

Herring sperm DNA was added to the buffers as indicated in Table 1:

TABLE 1

| | |
|---|---|
| 1 | 1 M guanidinium HCl, 20% ethanol [v/v], 20% [v/v] Triton X-100, 50 mM 2-morpholinoethanesulfonic acid (MES), pH 6 |
| 2 | 1 M guanidinium HCl, 20% [v/v] ethanol, 50 mM MES, pH 6 |
| 3 | 1 M guanidinium HCl, 50 mM MES, pH 6 |
| 4 | 3 M 1-butyl-3-methyl-imidazolium tetrafluoroborate, 50 mM sodium acetate, pH 4.5 |
| 5 | 1 M 1-butyl-3-methyl-imidazolium octylsulfate, 1 M guanidinium HCl, 50 mM MES, pH 6 |
| 6 | 1 M N-(1-butyl)-guanidinium hydrochloride, 50 mM sodium acetate, pH 4.5 |
| 7 | 0.5 M MgCl2, 50 mM MES, pH 6 |
| 8 | 1 M guanidinium HCl, 2 M MgCl2, 50 mM sodium acetate, pH 4.5 |
| 9 | 1 M guanidinium HCl, 1 M imidazole, pH 6 |
| 10 | 1 M guanidinium HCl, 0.1 M imidazole, pH 6 |

Figure 1:
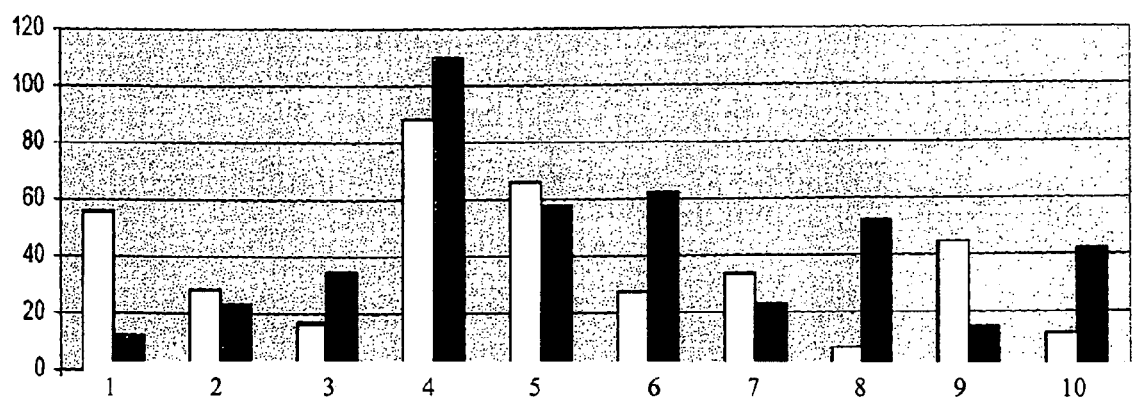
FIG. 1: Side-by-side adsorption of herring sperm DNA to two different types of glass fleece: Type A represented by the white bars, and type B represented by the black bars. The ordinate indicates the amount of adsorbed DNA onto the surface of the glass fleece. The pairs of bars are numbered and correspond to the respective adsorption buffers described in Table 1 of Example 2.

500 µl of each solution was loaded on spin columns. Further steps were performed as described in Example 1. Results are depicted on FIG. 1.

Example 3

Adsorption of 50 µg Calf Thymus DNA to Glass Fleece Under Different Conditions

Calf thymus DNA was used at a concentration of 50 µg DNA/500 µl buffer. The DNA was added to the buffers as indicated in Table 2:

TABLE 2

| | |
|---|---|
| 1 | 1 M guanidinium HCl, 50 mM MES, pH 6 |
| 2 | 1 M guanidinium HCl, 10% [v/v] ethanol, 50 mM MES, pH 6 |
| 3 | 1 M guanidinium HCl, 20% [v/v] ethanol, 50 mM MES, pH 6 |
| 4 | 1 M guanidinium HCl, 40% [v/v] ethanol, 50 mM MES, pH 6 |
| 5 | 1 M 1-butyl-3-methyl-imidazolium tetrafluoroborate, pH 4.5 50 mM sodium acetate |
| 6 | 1 M 1-butyl-3-methyl-imidazolium tetrafluoroborate, 50 mM MES, pH 6 |
| 7 | 1 M N-1-(2-methoxyethyl)-guanidinium hydrochloride, 50 mM MES, pH 6 |
| 8 | 2 M N-1-(2-methoxyethyl)-guanidinium hydrochloride, 50 mM MES, pH 6 |
| 9 | 3 M N-1-(2-methoxyethyl)-guanidinium hydrochloride, 50 mM MES, pH 6 |

Figure 2:
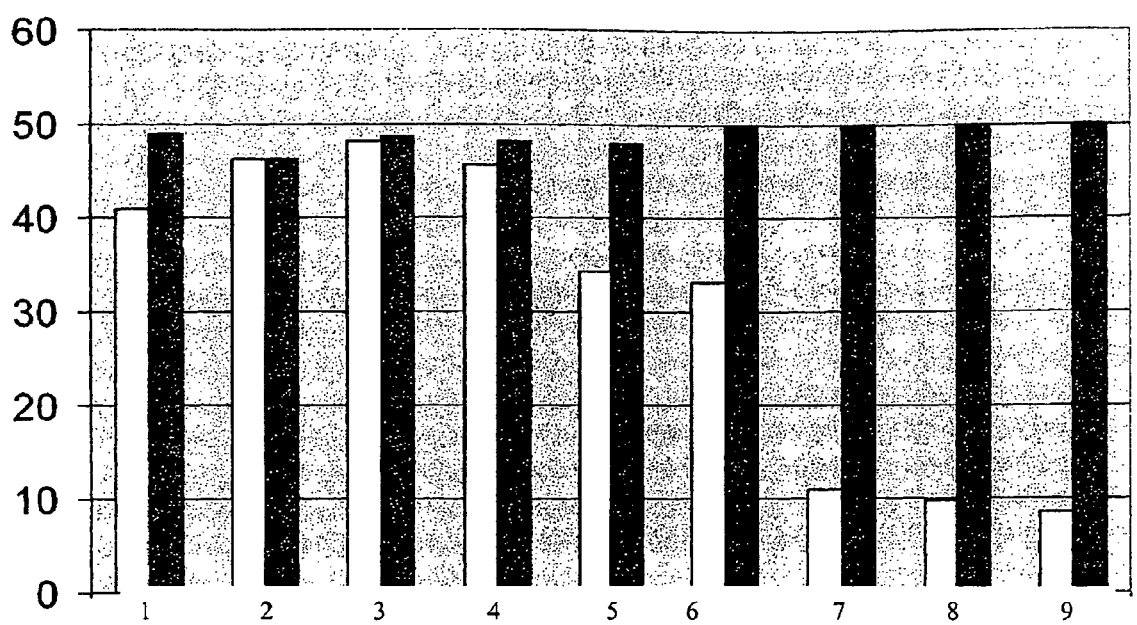
FIG. 2: Binding of calf thymus DNA under different conditions to spin columns (a) represented by white bars, glass fleece provided in the spin columns of the kit by Roche Applied Science, Roche Diagnostics GmbH Mannheim, Cat. No. 11796828; (b) represented by black bars, glass fleece provided in the spin columns of the kit by Macherey & Nagel (Cat. No. 740951.50, Lot: 407/001). The ordinate indicates the amount of adsorbed DNA onto the columns. The pairs of bars are numbered and correspond to the respective adsorption buffers described in Example 3, Table 2.

500 µl of each solution was loaded on spin columns. Further steps were performed as described in Example 1. Results are depicted on FIG. 2.

Example 4

Adsorption of 100 µg Calf Thymus DNA to Glass Fleece Under Different Conditions

Calf thymus DNA was used at a concentration of 100 µg DNA/500 µl buffer. The DNA was added to the buffers as indicated in Table 3:

TABLE 3

| | |
|---|---|
| 1 | 1 M guanidinium HCl, 50 mM MES, pH 6 |
| 2 | 1 M guanidinium HCl, 10% [v/v] ethanol, 50 mM MES, pH 6 |
| 3 | 1 M guanidinium HCl, 20% [v/v] ethanol, 50 mM MES, pH 6 |
| 4 | 1 M guanidinium HCl, 40% [v/v] ethanol, 50 mM MES, pH 6 |
| 5 | 1 M 1-butyl-3-methyl-imidazolium tetrafluoroborate, 50 mM sodium acetate, pH 4.5 |
| 6 | 1 M 1-butyl-3-methyl-imidazolium tetrafluoroborate, 50 mM MES, pH 6 |

Figure 3:
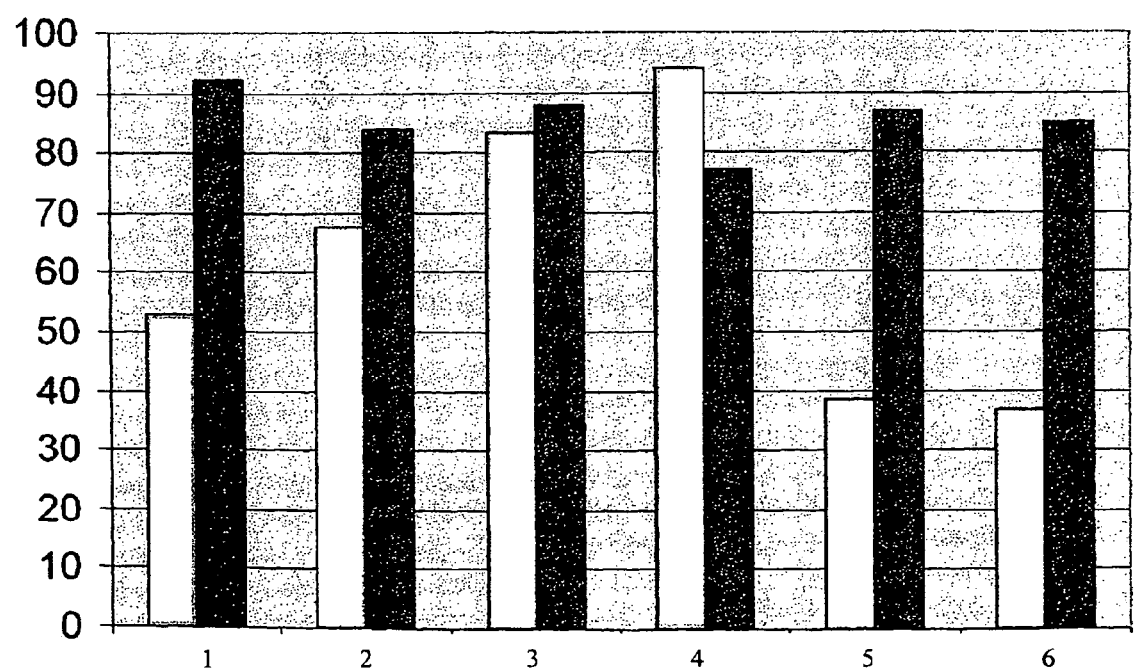
FIG. 3: Binding of calf thymus DNA under different conditions to spin columns (a) represented by white bars, glass fleece provided in the spin columns of the kit by Roche Applied Science, Roche Diagnostics GmbH Mannheim, Cat. No. 11796828; (b) represented by black bars, glass fleece provided in the spin columns of the kit by Macherey & Nagel (Cat. No. 740951.50, Lot: 407/001). The ordinate indicates the amount of adsorbed DNA which was eluted from the columns. The pairs of bars are numbered and correspond to the respective adsorption buffers described in Example 4, Table 3.

500 µl of each solution was loaded on spin columns. Further steps were performed as described in Example 1. Results are depicted on FIG. 3.

Example 5

Adsorption of RNA to Glass Fleece Under Different Conditions

RNA (see Example 1) was used at a concentration of 79 µg RNA/500 µl buffer. The RNA was added to the buffers as indicated in Table 4:

TABLE 4

| | |
|---|---|
| 1 | 1 M 1-butyl-3-methyl-imidazolium tetrafluoroborate, 50 mM sodium acetate, pH 4.5 |
| 2 | 2 M 1-butyl-3-methyl-imidazolium tetrafluoroborate, 50 mM MES, pH 6 |
| 3 | 3 M 1-butyl-3-methyl-imidazolium tetrafluoroborate, 50 mM MES, pH 6 |

Figure 4:
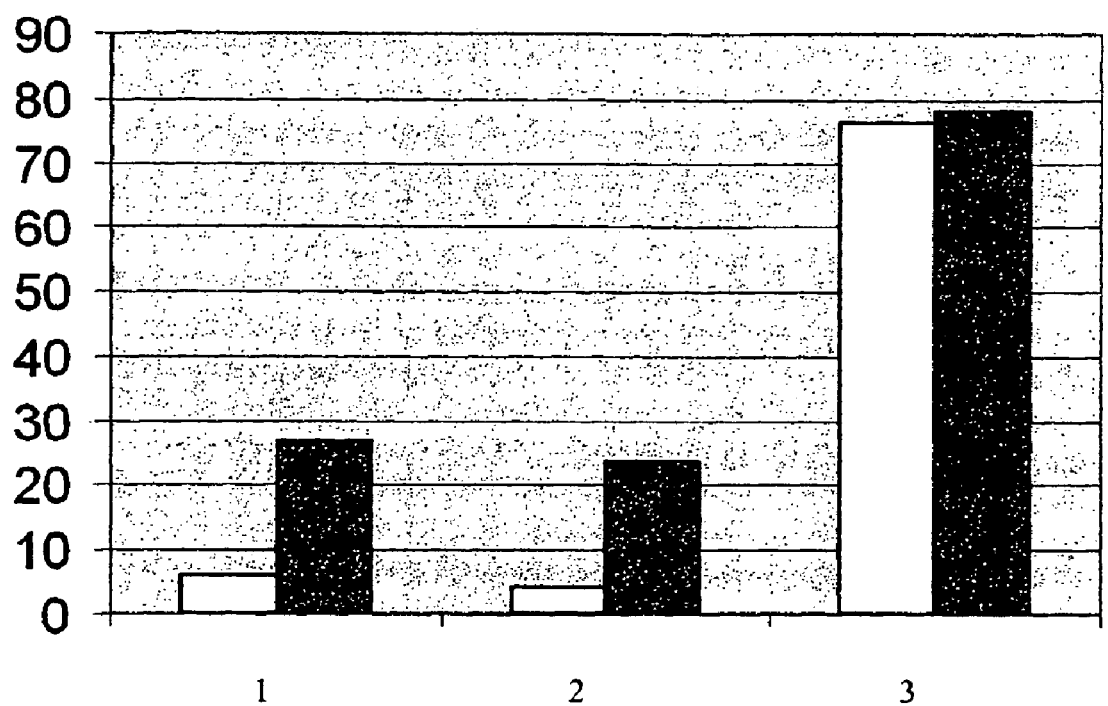
FIG. 4: Binding of yeast RNA under different conditions to spin columns (a) represented by white bars, glass fleece provided in the spin columns of the kit by Roche Applied Science, Roche Diagnostics GmbH Mannheim, Cat. No. 11796828; (b) represented by black bars, glass fleece provided in the spin columns of the kit by Macherey & Nagel (Cat. No. 740951.50, Lot: 407/001). The ordinate indicates the amount of adsorbed RNA which was eluted from the columns. The pairs of bars are numbered and correspond to the respective adsorption buffers described in Example 5, Table 4.
Figure 5:
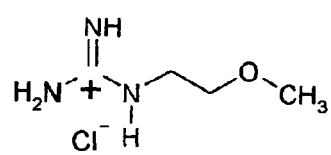
FIG. 5: Structures of (A) N-1-(2-methoxyethyl)-guanidinium hydrochloride; (B) N-(1-butyl)-guanidinium hydrochloride; (C) 1-butyl-3-methyl-imidazolium tetrafluoroborate, (D) 3-methyl-1-[4-(3-methyl-3-H!-benzimidazol-1-ium)-but-1-yl]-3H-benzimidazolium-di(toluoylsulfat)
Figure 5:
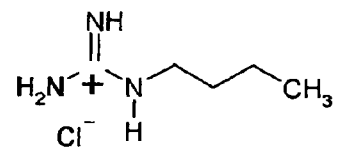
Figure 5:
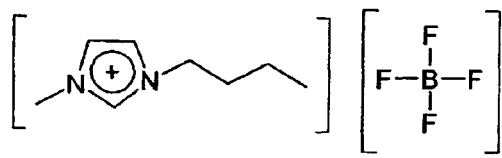
Figure 5:
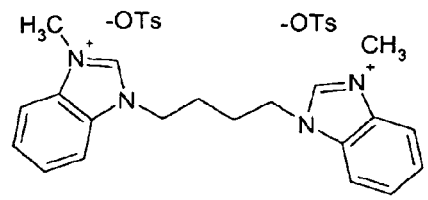

500 µl of each solution was loaded on spin columns. Further steps were performed as described in Example 1. Results are depicted on FIG. 4.

Example 6

Adsorption of 50 µg Calf Thymus DNA to Magnetically Attractable Glass Particles The magnetic particles were used from a MagNA Pure LC DNA isolation kit—large volume—from Roche Applied Science, Roche Diagnostics GmbH Mannheim, Cat. No. 03310515. The particles were suspended in isopropanol (60 mg/ml).

Calf thymus DNA was used at a concentration of 50 µg DNA/500 µl buffer. The DNA was added to the buffers as indicated in Table 5. Each sample was mixed with 100 µl of the particle suspension for 30 sec at room temperature.

Subsequently, the particles were immobilized by means of a magnetic field and separated from the liquid phase. The particles were washed once with 500 µl of a first aqueous washing buffer consisting of 5 M guanidinium HCl, 38% [v/v] ethanol, 20 mM Tris HCl, pH 6.6 and twice with 500 µl of a second aqueous washing buffer consisting of 100 mM NaCl, 50% [v/v] ethanol, 10 mM Tris HCl, pH 7.4. Each wash was performed by removing the magnetic field followed by suspending the particles in the respective wash buffer. In order to remove wash buffer, the particles were immobilized again by means of a magnetic field and separated from the liquid phase.

After the last washing step, adsorbed DNA was eluted from the particles by adding to the particles 500 µl elution buffer (10 mM Tris HCl, pH 8 in water) and agitating the particles in the elution buffer by vortexing vigorously. Subsequently, the particles were sedimented by centrifugation and the DNA-containing supernatant was recovered.

For photometric determination of DNA in the supernatant, a sample (100 µl) was taken from each eluate and, a 1:10 dilution was made with water, and the nucleic acid concentration was determined by measuring the extinction at 260 nm wavelength.

Table 5 indicates the compositions of the adsorption buffers used as well as the amount of DNA (in µg) eluted from the particles in each experiment.

TABLE 5

| | buffer composition | DNA (in µg) |
|---|---|---|
| 1 | 4.5 M guanidinium thiocyanate, 20% [v/v] Triton X-100, 50 mM Tris HCl, pH 6, 0.1% (w/v) bromophenol blue | 35.8 |
| 2 | 4.5 M guanidinium thiocyanate, 50 mM Tris HCl, pH 6 | 3.5 |
| 3 | 4.5 M guanidinium thiocyanate, 1 M 1-butyl-3-methyl-imidazolium tetrafluoroborate, 50 mM Tris HCl, pH 6 | 24 |
| 4 | 4.5 M guanidinium thiocyanate, 0.1 M 1-butyl-3-methyl-imidazolium tetrafluoroborate, 50 mM Tris HCl, pH 6 | 1.5 |
| 5 | 1 M guanidinium thiocyanate, 1 M 1-butyl-3-methyl-imidazolium tetrafluoroborate, 50 mM MES, pH 6 | 4 |
| 6 | 3M 1-butyl-3-methyl-imidazolium tetrafluoroborate, 50 mM MES, pH 6 | 28 |
| 7 | 4.5 M guanidinium thiocyanate, 0.15 M3-methyl-1-[4-(3-methyl-3-H-benzimidazol-1-ium)-but-1-yl]-3H-benzimidazolium-di(toluylsulfat), 50 mM MES, pH 6 | 12.4 |
| 8 | 3 M 1-butyl-3-methyl-imidazolium thiocyanate, 50 mM MES, pH 6 | 72 |

Example 7

Adsorption of Different Amounts of Calf Thymus DNA to Glass Fleece

A solution containing calf thymus DNA was prepared according to Example 1. The DNA was adsorbed onto glass fleece in the presence of an ionic liquid or guanidinium thiocyanate. The substances which were tested are listed in Table 6. Each adsorption solution was buffered to a pH value of pH 6 using MES, Tris or acetate buffer (10-50 mM). Adsorption was effected by passing the adsorption solution through the glass fleece of a spin column, e.g., a HIGHPURE spin column. Amounts of 25 µg, 50 µg and 100 µg were applied.

DNA was quantified spectrophotometrically (a) before applying the adsorption solution to the spin columns and (b) in the flow-through after the adsorption solution was passed through the glass fleece.

The concentration of DNA in the adsorption solution was determined prior to the adsorption step using the PICO GREEN assay (Invitrogen, Cat. No. P7589). Furthermore, using the PICO GREEN assay, the residual DNA concentration in each adsorption buffer after being passed through the glass fleece (that is: after the adsorption step) was determined. Using these measurements, the relative amount of DNA bound to the solid phase was determined for each adsorption solution.

In addition, the DNA concentration in the eluate was determined, however using photometric determination at 260 nm.

The amount of nucleic acid adsorbed to the solid phase was determined by subtracting the nucleic acid concentration in the flow-through (i.e., after adsorption) from the nucleic acid concentration initially applied to the column.

TABLE 6

| | substance | conc. in adsorption solution | amount of DNA applied to glass fleece (µg) | amount of DNA bound to glass fleece (µg) | amount of DNA in flow-through (µg) |
|---|---|---|---|---|---|
| | guanidinium thiocyanate | 1 M | 100 | 83.69. | 40.5 |
| | | | 50 | 49.86 | 34.2 |
| | | | 25 | 25.0 | 22.6 |
| 1 | 1-ethyl-3-methyl imidazolium ethylsulfate | 1 M | 100 | 86.2 | 58.5 |
| | | | 50 | 43.6 | 31.2 |
| | | | 25 | 24.9 | 19.2 |
| 2 | 1-butyl-3-methyl imidazolium ethylenglycol-monomethylether-sulfate | 1 M | 100 | 71.2 | 43.5 |
| | | | 50 | 46.9 | 29.2 |
| | | | 25 | 24.9 | 19.6 |

TABLE 6-continued

|   | substance | conc. in adsorption solution | amount of DNA applied to glass fleece (µg) | amount of DNA bound to glass fleece (µg) | amount of DNA in flow-through (µg) |
|---|---|---|---|---|---|
| 3 | 1-butyl-pyridinium chloride | 1 M | 100 | 93.4 | 60.8 |
|   |   |   | 50 | 49.9 | 47.5 |
|   |   |   | 25 | 25 | 22.0 |
| 4 | 3-methyl-1-[4-(3-methyl-3H-benzimidazol-1-ium)-but-1-yl]-3H-benzimidazolium-di(toluylsulfate) | 0.15 M | 100 | 85.5 | 49.5 |
|   |   |   | 50 | 49.9 | 30.5 |
|   |   |   | 25 | 25 | 25.4 |
| 5 | n-butane-1,4-diguanidinium-sulfate | 0.037 M | 100 | 79.9 | 49.5 |
|   |   |   | 50 | 49.7 | 31.2 |
|   |   |   | 25 | 25.0 | 24.9 |

It was additionally observed that higher concentrations (2M, 3M, and 4M) of the ionic liquids shown in the table produced comparable results.

What is claimed is:

1. A method for purifying a nucleic acid comprising the steps of:
providing a solid phase capable of reversibly binding the nucleic acid;
providing a sample containing the nucleic acid;
providing a solution containing a water-soluble salt which is liquid at room temperature (ionic liquid) and which comprises an organic cation selected from either the group consisting of N-(1-butyl)-guanidinium, N-1-(2-methoxyethyl)-guanidinium, and n-butane-1,4-diguanidinium, or the group consisting of 1-ethyl-3-methyl imidazolium, 1-butyl-3-methyl-imidazolium, 3-methyl-1-[4-(3-methyl-3-H-benzimidazol-1-ium)-but-1-yl]-3H-benzimidazolium-di(toluylsulfat), and 1-butyl-pyridinium;
providing an aqueous buffer;
contacting the provided components under conditions whereby the nucleic acid is adsorbed to the solid phase;
separating the solid phase with the adsorbed nucleic acid from the solution;
eluting the nucleic acid from the solid phase, thereby purifying the nuclec acid.

2. A method to enhance the effect of a chaotropic compound on the adsorption of a nucleic acid to a solid phase, the method comprising the steps of:
providing an aqueous adsorption solution comprising the nucleic acid, a buffer, and a chaotropic agent,
adding to the adsorption solution an effective amount of a water-soluble salt which is liquid at room temperature (ionic liquid) and which comprises an organic cation selected from either the group consisting of N-(1-butyl)-guanidinium, N-1-(2-methoxyethyl)-guanidinium, and n-butane-1,4-diguanidinium, or the group consisting of 1-ethyl-3-methyl imidazolium, 1-butyl-3-methyl-imidazolium, 3-methyl-1-[4-(3-methyl-3-H-benzimidazol-1-ium)-but-1-yl]-3H-benzimidazolium-di(toluylsulfat), and 1-butyl-pyridinium,
thereby enhancing adsorption of the nucleic acid to the solid phase.

3. A composition for adsorbing a nucleic acid to a solid phase, the composition comprising a water-soluble salt which is liquid at room temperature (ionic liquid) and comprises an organic cation selected from the group consisting of N-(1-butyl)-guanidinium, N-1-(2-methoxyethyl)-guanidinium, and n-butane-1,4-diguanidinium.

* * * * *